(12) United States Patent
Vanotti et al.

(10) Patent No.: US 8,574,885 B2
(45) Date of Patent: Nov. 5, 2013

(54) ANAMMOX BACTERIUM ISOLATE

(75) Inventors: Matias B. Vanotti, Florence, SC (US); Ariel A. Szogi, Florence, SC (US); Michael J. Rothrock, Jr., Bangor, ME (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 409 days.

(21) Appl. No.: 13/013,874

(22) Filed: Jan. 26, 2011

(65) Prior Publication Data
US 2011/0180476 A1    Jul. 28, 2011

Related U.S. Application Data (60) Provisional application No. 61/298,952, filed on Jan. 28, 2010.

(51) Int. Cl.
*C12N 1/20*    (2006.01)

(52) U.S. Cl.
USPC .................................. 435/252.1; 210/630

(58) Field of Classification Search
None
See application file for complete search history.

(56) References Cited

PUBLICATIONS van Niftrik et al., Journal of Bacteriology, Jan. 2008, p. 708-717 vol. 190, No. 2.*

* cited by examiner

*Primary Examiner* — Irene Marx
(74) *Attorney, Agent, or Firm* — John Fado; Albert Y. Tsui; Lesley Shaw (57) ABSTRACT

Disclosed is an isolated bacterium strain *Candidatus Brocadia caroliniensis*, having Accession Deposit Number NRRL B-50286. The strain is capable of oxidizing ammonium and releasing di-nitrogen gas.

4 Claims, 10 Drawing Sheets

ATGCAAGTCGAACGAGGGAGCATTCCGAAAGGGGTGCAAACCGAGTGGCGTAAGGGTGAGTAATGCA
TTGATAACCTACCTTCGAGTATGAGAATAACAACGTTCCAAGCAATTGGGGCTACCGAAAGGGTTGCT
AATACTCAATAAAACTATTATTGCTTCGGTGGTGATAGTCAAATAGGCGGAATCGAAAGGTTCCACTT
GCTTGAGGAGGGGTCAATGTCCTATCAGCTAGTTGGCAGGGTAATGGCCTACCAAGGCGAAGACGGG
TAGCCGGCCTGAGAGGGTGGGTCGGCCACACTGGGACTGAGACACTGCCCAGACTCCTACGGGAGGC
TGCAGTCGAGAATCTTTCGCATGCCCGAAAGGGTGACGAAGCGACGCCGCGCTGCGGGAAGAAGGCC
TTCGGGTTGTAAACCGCTGTCGGGAGTTAAGAAGTGCAGGGATGTTAATAGCATCCCTGCTTGACTAA
GGCTCCGGAGGAAGCCACGGCTAACTCTGTGCCAGCAGCCGCGGTAATACAGAGGCGGCAAGCGTTG
TTCGGAATTATTGGGCGTAAAGAGCACGTAGGCGGCCGTGTAAGTCGGTTGTGAAAGCCTTCCGCTCA
ACGGAAGGACGGCATCCGATACTGCATGGCTCGAGTGCGGGAGGGGAGAGTGGAACTTCTGGTGGAG
CGGTGAAATGCGTAGATATCAGAAGGAACACCGGCGGCGAAGGCGACTCTCTGGTCCGTAACTGACG
CTGAGTGTGCGAAAGCTAGGGGAGCAAACGGGATTAGATACCCCGGTAGTCCTAGCCGTAAACGATG
GGCACTAAGTAGAGGGGTTTTGATTATCTCTCTGCCGGAGCTAACGCATTAAGTGCCCCGCCTGGGGA
GTACGGCCGCAAGGCTAAAACTCAAAAGAATTGACGGGGGCTCGCACAAGCGGTGGAGCATGTGGCT
TAATTCGATGCAACGCGAAGAACCTTACCGGGGTTTGACATGGTAGAAGTAGGAGCCCGAAAGGGTA
ACGAACGGTATCCAGTCCGTAACTATCACAGGTGTTGCATGGCTGTCGTCAGCTCGTGTCGTGAGACG
TTGGGTTAAGTCCCCTAACGAGCGAAACCCTTGTCTTTAGTTGCCAACGGTCATGCTGGGCACTCTAAA
GAGACTGCCGTCGTCAAGACGGAGGAAGGTGGGGATGACGTCAAGTCATCATGGCCCTTATATCCCGG
GCTGCACACGTGCTACAATGGTCGATACAAAGGGATGCTAAGCCGTAAGGCGGAGCGAAACCCAGAA
AGTCGATCCCAGTTCAGATTGGAGGCTGAAACCCGCCTCCATGAAGTAGGAATCGCTAGTAATCGCGG
ATCAGCTACGCCGCGGTGAATATGTTCCCGAGCCTTGTACACACCGCCCGTCAAGCCACCCAAGCAAG
ATGCACCCAAAATCACCGGCCTAACCTGCAAAGGAGGGAAGTGCTTAAGGTGTGTTTTGTGAGGAGG
ACTA

SEQ. ID. NO. 1

FIG. 10

SEQUENCE LISTING

<160> NUMBER OF SEQ ID NOS: 1

<210> SEQ ID NO 1
<211> LENGTH: 1489
<212> TYPE: DNA
<213> ORGANISM: Brocadia caroliniensis

<400> SEQUENCE: 1

```
atgcaagtcg aacgagggag cattccgaaa ggggtgcaaa ccgagtggcg taagggtgag    60
taatgcattg ataacctacc ttcgagtatg agaataacaa cgttccaagc aattggggct   120
accgaaaggg ttgctaatac tcaataaaac tattattgct tcggtggtga tagtcaaata   180
ggcggaatcg aaaggttcca cttgcttgag gaggggtcaa tgtcctatca gctagttggc   240
agggtaatgg cctaccaagg cgaagacggg tagccggcct gagagggtgg gtcggccaca   300
ctgggactga gacactgccc agactcctac gggaggctgc agtcgagaat ctttcgcatg   360
cccgaaaggg tgacgaagcg acgccgcgct gcgggaagaa ggccttcggg ttgtaaaccg   420
ctgtcgggag ttaagaagtg cagggatgtt aatagcatcc ctgcttgact aaggctccgg   480
aggaagccac ggctaactct gtgccagcag ccgcggtaat acagaggcgg caagcgttgt   540
tcggaattat tgggcgtaaa gagcacgtag gcggccgtgt aagtcggttg tgaaagcctt   600
ccgctcaacg gaaggacggc atccgatact gcatggctcg agtgcgggag gggagagtgg   660
aacttctggt ggagcggtga aatgcgtaga tatcagaagg aacaccggcg gcgaaggcga   720
ctctctggtc cgtaactgac gctgagtgtg cgaaagctag gggagcaaac gggattagat   780
accccggtag tcctagccgt aaacgatggg cactaagtag aggggttttg attatctctc   840
tgccggagct aacgcattaa gtgccccgcc tggggagtac ggccgcaagg ctaaaactca   900
aaagaattga cggggctcg cacaagcggt ggagcatgtg gcttaattcg atgcaacgcg   960 aagaaccta ccggggtttg acatggtaga agtaggagcc cgaaagggta acgaacggta  1020
tccagtccgt aactatcaca ggtgttgcat ggctgtcgtc agctcgtgtc gtgagacgtt  1080
gggttaagtc ccctaacgag cgaaacccct gtctttagtt gccaacggtc atgctgggca  1140
ctctaaagag actgccgtcg tcaagacgga ggaaggtggg gatgacgtca agtcatcatg  1200
gcccttatat cccgggctgc acacgtgcta caatggtcga tacaaaggga tgctaagccg  1260
taaggcggag cgaaacccag aaagtcgatc ccagttcaga ttggaggctg aaacccgcct  1320
ccatgaagta ggaatcgcta gtaatcgcgg atcagctacg ccgcggtgaa tatgttcccg  1380
```

```
agccttgtac acaccgcccg tcaagccacc caagcaagat gcacccaaaa tcaccggcct    1440
aacctgcaaa ggagggaagt gcttaaggtg tgttttgtga ggaggacta               1489
```

ANAMMOX BACTERIUM ISOLATE

CROSS-REFERENCE TO RELATED APPLICATION

This present application claims priority under 35 U.S.C. §119(e) to U.S. Provisional Ser. No. 61/298,952, which was filed on Jan. 28, 2010, the disclosure of which is hereby incorporated by reference.

FIELD OF THE INVENTION

Disclosed herein is for a novel bacterium strain *Candidatus Brocadia caroliniensis*, having Accession Deposit Number NRRL B-50286 and the characteristics of oxidizing ammonia and releasing di-nitrogen under anaerobic conditions.

BACKGROUND OF INVENTION

The use of bacteria for removal of nitrogen from wastewaters features a combination of nitrification and denitrification processes. (Tchobanoglous, G., et al., (1991) Wastewater Engineering: Treatment, Disposal, and Reuse. Boston, Mass.: Irwin/McGraw-Hill). A disadvantage of the nitrification is that large amounts of oxygen and energy are required to convert all the ammonium ($NH_4^+$) into nitrate ($NO_3^-$). The subsequent biological reduction of nitrate to nitrogen gas ($N_2$) requires heterotrophic bacteria that utilize a carbon source to convert $NO_3^-$ into $N_2$ gas typically under anoxic conditions (Furukawa, K., et al., (2009) Innovative treatment system for digester liquor using anammox process. *Bioresour. Technol.* 100:5437-5443). Given the high energy costs pertaining to nitrification and the addition of carbon source pertaining to the denitrification process, there is a need to develop a more economical treatment system for effluents containing high ammonium concentrations.

An alternative biological process to $N_2$ production via nitrite ($NO_2^-$) reduction is via anaerobic ammonia oxidation. Anaerobic ammonia oxidation is also referred to as anammox. The anammox process was recognized in a wastewater treatment system based on N mass balance (Mulder, A., et al., (1995) Anaerobic ammonium oxidation discovered in a denitrifying fluidized bed reactor. *FEMS Microbiol. Ecol.* 16:177-184). In the anammox process, under anaerobic and autotrophic conditions, ammonium ($NH_4^+$) serves as the electron donor using nitrite ($NO_2^-$) as the electron acceptor resulting in production of harmless di-nitrogen ($N_2$) gas (Strous, M., et al., (1998) The sequencing batch reactor as a powerful tool for the study of slowly growing anaerobic ammonium-oxidizing microorganisms. *Appl. Micobiol. Biotechnol.* 50:589-596; Jetten, M. S. M., et al., (1999) The anaerobic oxidation of ammonium. *FEMS Microbiol. Rev.* 22:421-437). The complete ammonia removal process, or deammonification, entails two sequential reactions: partial nitritation ($NH_4^+ + 1.5\ O_2 \rightarrow NO_2^- + H_2O + 2\ H^+$) and anammox ($NH_4^+ + 1.32\ NO_2^- \rightarrow 1.02\ N_2 + 0.26\ NO_3^- + 2\ H_2O$). Although this anammox equation does not consider other reactants related to cell synthesis (Dongen, van L. G. J. M., et al., (2001) The SHARON-Anammox process for the treatment of ammonium rich wastewater. *Water Sci. Technol.* 44:154-160), it has been used to describe the basic anammox process. The partial nitritation can be accomplished with the inhibition of nitrite oxidizing bacteria through limited oxygen supply (Kuai, L. P., et al., (1998) *Applied and Environmental Microbiology* 64:4500-4506), the use of high process temperatures, (Dongen, van L. G. J. M., et al., (2001) The Combined Sharon/Anammox Process, STOWA report, IWA Publishing, London) or enhancing free-ammonia concentration as a result of high pH and ammonium concentrations (Anthoniesen, A. C., et al., (1976) Inhibition of nitrification by ammonia and nitrous acid. *Journal WPCF* 48(5):835-852).

Compared to conventional nitrification-denitrification, these combined partial nitritation and anammox reactions save more than 50% of the oxygen supply for nitrification and 100% of the external organic carbon source for denitrification (Furukawa, K., et al., (2009) Innovative treatment system for digester liquor using anammox process. *Bioresour. Technol.* 100:5437-5443). This leads to a significant reduction in energy needs of treatment and a decrease in operational costs. In addition, by-products of anammox do not include greenhouse gases. The isolation of anammox microorganisms adapted to animal wastewater environments is of significant importance to farming systems inasmuch as excess ammonia in modern livestock production is a global problem and the use of conventional biological N removal methods is limited by cost. Thus an economical anammox based treatment is needed to facilitate greater adoption of advanced wastewater treatment technologies by wastewater facilities.

All microorganisms found responsible for the anammox reaction have been extremely difficult to isolate and no pure cultures exist (Megonigal, J. P., et al., (2005) Anaerobic metabolism: Linkages to trace gases and aerobic processes. In *Biogeochemistry Vol.* 8, 317-424). One of the difficulties in isolating bacteria that perform anammox process stems from the fact that the bacteria have a slow growth rate, wherein the doubling growth rate can take approximately two weeks. Another difficulty is isolating anammox bacteria in a natural environment. Yet another difficulty is to develop a specific autotrophic enrichment media that eliminates initial growing inhibition of the particular bacterial strain while mimicking natural environment conditions.

The enrichment of anammox microorganisms has been reported in several bioreactor studies (Egli, K., et al., (2001) Enrichment and characterization of an anammox bacterium from a rotating biological contactor treating ammonium-rich leachate. *Arch. Microbiol.* 60:135-153; Strous, M., J et al., (1999) Missing littroph identified as a new planctomycete. *Nature,* 400:446-449; Toh, S. K., et al., (2002) Enrichment of autotrophic anaerobic ammonium-oxidizing consortia from various wastewaters. *Microb. Ecol.* 43:154-167; Nkajima, J., et al., (2008) Enrichment of anammox bacteria from marine environment for the construction of a bioremediation reactor. *Appl. Microbiol. Biotechnol.* 77:119-116). Common to all these studies, anammox microorganisms were identified as members of the order Planctomycetales, a major division of the Bacteria, using molecular techniques such 16 rDNA and in situ hybridization (Schmid, M. C., et al., (2005) Biomarkers for insitu detection of anaerobic ammonium-oxidizing (anammox) bacteria. *Appl. Environm. Microbiol.* 71:1677-1684).

It is therefore an object of the invention to isolate a bacterium strain that utilizes the anammox process. It is contemplated that the bacterium strain would be used as a biotreatment of wastewaters containing ammonia.

These and other objects of the invention will become apparent as a detailed description of the representative embodiments is disclosed infra.

BRIEF SUMMARY OF THE INVENTION

Disclosed herein is an isolated anaerobic ammonium oxidation bacterium capable of oxidizing ammonium and releasing di-nitrogen gas having Accession Deposit Number NRRL B-50286. The bacterium is capable of reactivation after lyophilization. The bacterium has the ribosomal DNA disclosed in SEQ. ID. NO. 1.

Also disclosed is a method for treating wastewater containing ammonia and nitrite, the method comprising: (a) providing a reactor having an inlet for receiving said wastewater thereto and an outlet for discharge of effluent liquid therefrom, (b) providing bacterium strain NRRL B-50286 as a organism for reducing ammonia in said wastewater to di-nitrogen; and (c) adding said bacterium strain to said wastewater within said reactor. Also disclosed is a method for treating wastewater with bacterium strain NRRL B-50286 in conjunction with a one-stage reactor, two-stage reactor, or multiple stage reactors.

Also disclosed is a method for treating wastewater containing ammonia, the method comprising: (a) providing a partial nitritation reactor to form an effluent liquid containing nitrite and ammonia and having an inlet for receiving said wastewater thereto and an outlet for discharge of effluent liquid therefrom, (b) an anammox reactor in fluid communication with said partial nitritation reactor, (c) providing bacterium strain NRRL B-50286 as a organism for reducing ammonia to di-nitrogen from the liquid effluent from said partial nitritation reactor; and (c) adding said bacterium strain to said wastewater within said anammox reactor.

Also disclosed is a method for treating wastewater containing ammonia, the method comprising: (a) providing a reactor having an inlet for receiving said wastewater thereto and an outlet for discharge of effluent liquid therefrom, (b) providing bacterium strain NRRL B-50286 as a organism for reducing ammonia in said wastewater to di-nitrogen; (c) adding said bacterium strain to said wastewater within said reactor; (d) adding nitrosomonas spp within said reactor, and (e) providing partial aeration to the same reactor.

Also disclosed is a wastewater treatment composition, the composition comprising: (a) the bacterium having Accession Deposit Number NRRL B-50286 in amounts effective to reduce levels of ammonia and release di-nitrogen; and (b) a suitable carrier.

BRIEF DESCRIPTION OF THE DRAWING

FIGS. 5 A-C are graphs of stoichiometric ratios of revived anammox bacterium NRRL B-50286 after being preserved for a period of four months in either (A) nitrate solution at 4° C., (B) lyophilized skim milk media (freezing temperature=−60° C.), or (C) lyophilized skim milk media using liquid nitrogen (freezing temperature=−200° C.).

DEPOSIT OF BIOLOGICAL MATERIAL

The isolate identified as a strain of *Candidatus Brocadia caroliniensis* based on 16S ribosomal DNA gene sequencing. Sequence of *Candidatus Brocadia caroliniensis* was 96% similar to the sequences of *Candidatus "Brocadia"* sp. having GenBank Accession numbers AM285341. A strain of *Brocadia caroliniensis* was deposited on May 12, 2009, under the provisions of the Budapest Treaty in the Agricultural Research Culture Collection (NRRL) at 1815N. University Street, Peoria, Ill., and has been assigned Accession No. NRRL B-50286.

Anammox Bacteria Characterization

Figure 1:
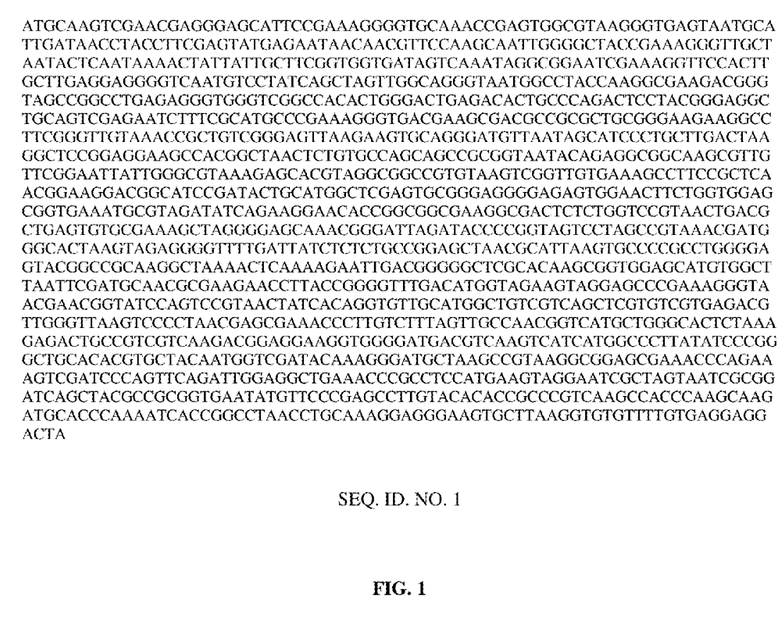
FIG. 1 is of the ribosomal DNA (16S) sequence of anammox bacterium NRRL B-50286.
Figure 4:
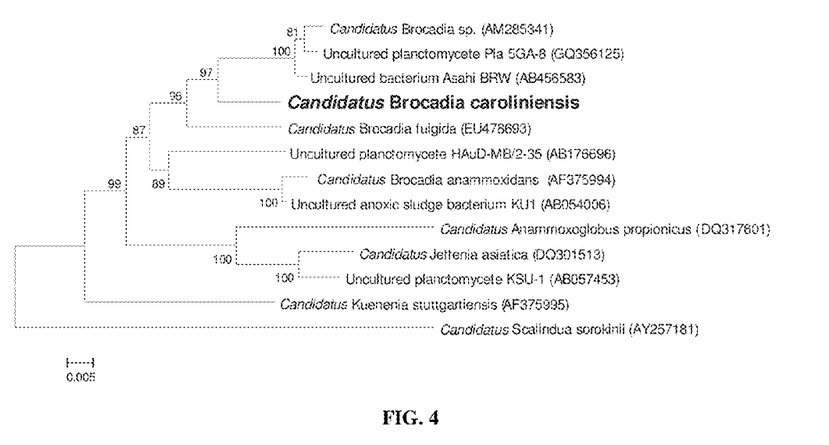
FIG. 4 is a bootstrapped (n=1000) Neighbor Joining phylogenetic tree of NRRL B-50286 identified as *Candidatus Brocadia caroliniensis* in relation to major genera of anammox bacterium found in the GenBank Database. The identifiers in the parentheses after the strain name represents the GenBank accession number. Numbers at the nodes of the tree represent the bootstrap values for that node, and the error bar at the bottom of the tree indicates the distance representative of 0.5% difference between sequences on the tree.

Analysis of the RFLP fingerprint patterns revealed that all but one recovered clone exhibited the same fingerprint pattern for all three restriction endonucleases (HaeIII, RsaI, Sau3AI), indicating that the anammox sludge was dominated by a single bacterium. The DNA sequence of the dominant bacterium is shown in FIG. 1. The closest matches for the dominant anammox clone from the GenBank Database are shown in Table 1. While the nearest match in the database (96%, based on DNA homology) was to an uncultured bacterium clone from an anammox reactor treating partially nitrified wastewater of the Asahi Breweries, Ltd., Japan, our clone sequence most closely matched (96-94% DNA similarity) known sequences from the *Candidatus Brocadia genera*, while being much less similar to the remaining anammox genera (<92%). The most similar defined *Candidatus Brocadia* species to our clone sequence was *Candidatus Brocadia fulgida* (96%) (Woebken et al., 2008). Phylogenetic analysis of our dominant anammox clone also revealed its putative assignment in the *Candidatus Brocadia genera* (FIG. 4, Bold Text). Due to the relatively low DNA sequence homology (≤96%, Table 1) and phylogenetic relationships (FIG. 4), we propose that the dominant bacteria in our anammox bioreactor is a novel species of the *Candidatus Brocadia genera*, and have named this novel anammox species *Candidatus Brocadia caroliniensis*.

TABLE 1

16S rDNA sequence homology between Candidatus "Brocadia caroliniensis" and anammox sequences from the GenBank Database.

| Matching Sequence | GenBank Accession Number | Percent Similarity to Candidatus "Brocadia caroliniensis" |
|---|---|---|
| Uncultured bacterium clone Asahi BRW | AB456583 | 96% |
| Candidatus "Brocadia" sp. | AM285341 | 96% |
| Candidatus "Brocadia fulgida" | EU478693 | 96% |
| Candidatus "Brocadia anammoxidans" | AF375994 | 94% |
| Candidatus "Jettenia asiatica" | DQ301513 | 92% |
| Candidatus "Kuenia stuttgartiensis" | AF375995 | 90% |
| Candidatus "Anammoxoglobus propionicus" | EU478694 | 90% |
| Candidatus "Scalindua sorokinii" | AY257181 | 86% |

DETAILED DESCRIPTION OF THE INVENTION

The present invention relates to a novel bacterium strain *Candidatus Brocadia caroliniensis*, having Accession Deposit Number NRRL B-50286 and the characteristics of oxidizing ammonia and releasing di-nitrogen.

Definitions

As used in the specification and claims, the singular form "a", "an" and "the" include plural references unless the context clearly dictates otherwise. For example, the term "a bacterium" includes a plurality of unicellular microorganisms of the same species.

As referred to herein, bacterium strain identified as NRRL B-50286 is also referred to as *Candidatus Brocadia caroliniensis*. The term "anammox" refers to conversion of ammonia and nitrite to di-nitrogen by anaerobic ammonium oxidizing bacteria. The term partial nitritation refers to the conversion of about half of the ammonia to nitrite by aerobic ammonium oxidizing bacteria, such as Nitrosomonas spp. The term deammonification refers to the complete ammonia removal from wastewater based on both partial nitritation and the anammox processes. Deammonification can be performed in two separate reactors (two-stage partial nitritation/anammox) or in a single reactor (one stage partial nitritation/anammox). The anammox process can be performed by treating nitrification effluent in either a one-stage reactor or a two stage reactor.

The novel bacterium strain *Candidatus Brocadia caroliniensis* of this invention may be used for the treatment of any wastewater contaminated with animal waste and/or having undesirable levels of ammonia, including municipal, industrial or agricultural wastewater. However, the invention is particularly suited for the treatment of wastewater collected from animal rearing or holding facilities, which typically comprises liquid slurries of manure in urine, or manure and/or urine mixed with water or aqueous treatment solutions, such as that used for flushing manure and urine from those facilities. The autotrophic nitrogen removal through partial nitritation and anammox reactions is used after the removal of biodegradable organic materials using biological oxygen demand (BOD) removal processes conventional in the art such as settling, membrane filtration, flocculation, oxidation, and anaerobic digestion. The bacterium composition and process may be used for the treatment of animal wastes generated by a variety of livestock, and domestic or wild animals, including but not limited to zoo animals, sheep, swine, poultry, goats, cattle, dairy cows, horses, ducks, or geese. However, the compositions and process are particularly suited to the treatment of animal wastes from animal containment facilities used for the large-scale rearing of dairy cows and the production of swine and cattle.

The anammox reaction using NRRL B-50286 may be conducted in a variety of reactor systems. Moreover, while the reaction will typically be conducted in a tank, it is understood that the reaction may be conducted in any vessel or reservoir used for wastewater storage provided that suitable conditions are provided to maintain a suitable anoxic environment under low dissolved oxygen (DO) level and the presence of ammonia ($NH_4^+$) and nitrite ($NO_2^-$) to support the growth and biological activity of the bacterium in the composition. By way of example and without being limited thereto, suitable systems include attached or suspended-growth bioreactors. In suspended-growth, the bacterium composition may be mixed with the wastewater by the agitation of the liquid. In a desirable form, the anammox bacterium is self-immobilized and agglomerated in individual granules preferably between the sizes of 1 mm to 5 mm.

Alternatively, in an attached-growth bioreactor, various solid support media are provided to allow bacterium in the composition to attach to the surface thereof. Suitable media include, but are not limited to trickling filters, rotating biological contactors, packed-bed reactors, and others known in the art. Yet another attached-growth bioreactor that is suitable for use herein is a fluidized or moving bed reactor. In this system, bio-carriers containing the bacterium remain suspended in the wastewater being treated, fluidized by the drag forces associated with the mixing of the water. The anammox bacterium may be entrapped in polymeric porous materials such as particles of polyvinyl alcohol (PVA), polyethylene glycol (PEG), or other polymer gels such as calcium alginate. The anammox bacterium may be attached forming biofilms in suspended carriers such as K1, K3, MiniChip, and Biofilm-Chip plastic carriers (AnoxKaldnes, Sweden). Fluidized bed reactors allow the populations of microorganisms to increase rapidly, thus reducing the time necessary for ammonia removal.

Figure 8:
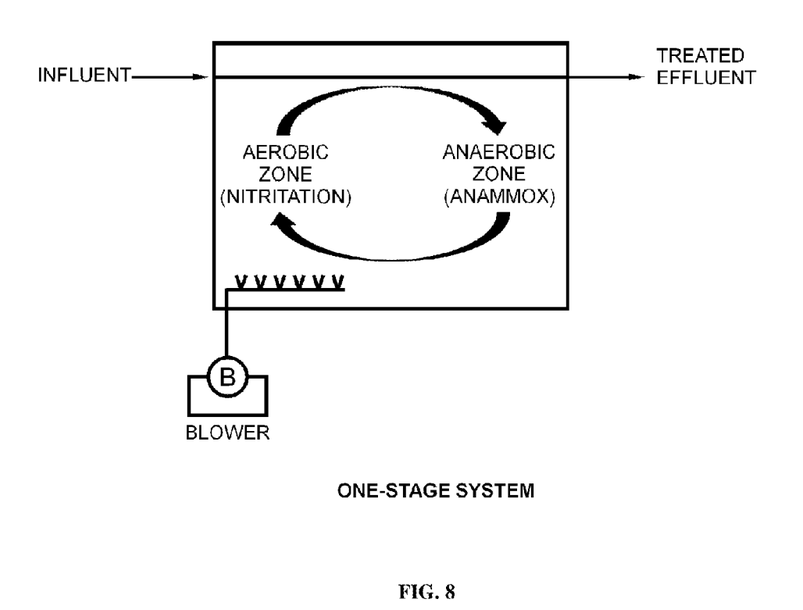
FIG. 8 is a schematic diagram for one-stage wastewater treatment system.
Figure 9:
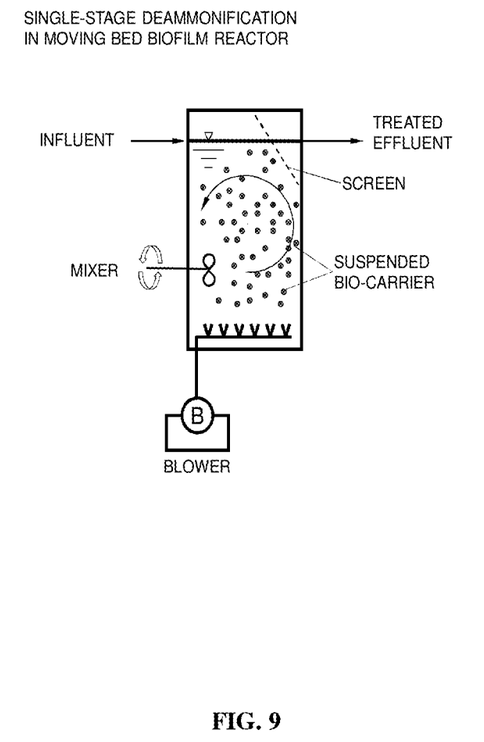
FIG. 9 is a schematic diagram for a one-stage deammonification process combining nitritation and anammox by bacterial biofilms attached to carriers using a single MBBR (Moving Bed Biofilm Reactor) reactor. Useful bacterial immobilization techniques include immobilized biomass entrapped in polymer gels, attached type on the surface of carriers, and self immobilized type in granular formations.

Although the anammox reaction using NRRL B-50286 may be employed in a stand-alone system for the conversion of ammonia and nitrite to di-nitrogen, preferably the anammox reaction is performed in conjunction with partial nitritation in a single reactor as depicted in FIGS. 8 and 9. The term partial nitritation refers to the conversion of about half of the ammonia to nitrite by aerobic ammonium oxidizing bacteria, such as *Nitrosomonas* spp. The term deammonification refers to the complete ammonia removal from wastewater based on both partial nitritation and anammox processes. Deammonification can be performed in two separate reactors (two-stage partial nitritation/anammox) or in a single reactor (one stage partial nitritation/anammox).

It is also contemplated that the anammox reaction using the bacterium NRRL B-50286 may be conducted in soil filtration systems provided that suitable conditions are provided to maintain a suitable anoxic environment under low dissolved oxygen (DO) level and the presence of ammonia ($NH_4^+$) and nitrite ($NO_2^-$) to support the growth and biological activity of the bacteria in the composition. In these soil filtration treatment systems, the anammox bacterium NRRL B-50286 would be introduced into soil media to convert ammonia and nitrite into nitrogen gas. The soil media would serve as bio-support for the bacteria. Examples of soil based filtration systems known in the art are related to overland flow (Szogi, et al., 2004, New Zealand J. Agric. Res. 47(4):439-448), constructed wetlands (Szogi et al., (2003) Soil Sci. Soc. Am. J. 67(6):1943-1951); (Martinez, J. et al., 1997, Journal of Agricultural Engineering Research, Volume 66, Issue 1, January, Pages 51-62) riparian buffers, and vegetative filters. An advantage in utilizing strain NRRL B-50286 in conjunction with soil filtration is systems is that ammonia and nitrite are removed without the emitting the greenhouse gas, nitrous oxide.

Enrichment of Anammox Bacteria

Anammox cultures were successfully established in three consecutive trials of bioreactors using continuous-flow unit processes and biomass carriers seeded with sludges of manure origin from swine farms located in North Carolina, USA. The sludge containing anammox bacteria were obtained from the two following sources: an aerobic nitrification tank treating anaerobically-digested swine manure and an anoxic denitrification tank treating liquid swine manure after solid-liquid separation. Laboratory bioreactors were seeded with the manure sludge after acclimation with potassium nitrate solution (100 mg $NO_3$—N/L) to remove endogenous carbon through biological denitrification using glass vessels. The solution was renovated weekly until nitrate analyses revealed denitrification inhibition due to lack of carbon in the sludge.

Figure 2:
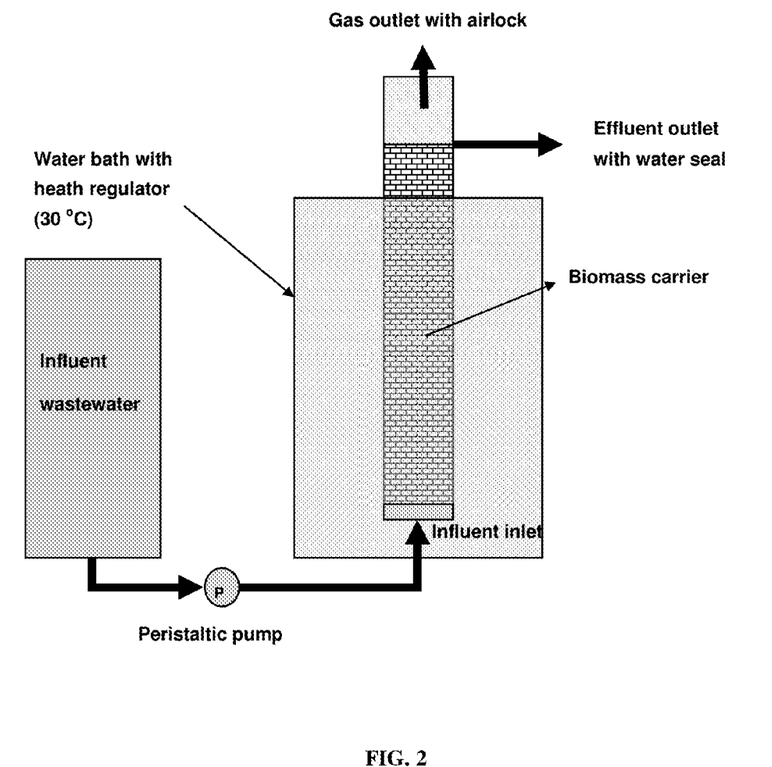
FIG. 2 is a schematic diagram of a 1-L bioreactor containing biomass carrier beads for immobilization and enrichment of the slow growth microorganisms.

Two sequential trials were conducted over a 5-year period to investigate conditions to isolate anammox bacteria from the swine sludges (3 years), and to optimize the anammox treatment in bioreactors (2 years). The bioreactors were operated in continuous flow and contained polyvinyl alcohol (PVA) hydrogel biomass carrier beads for immobilization and enrichment of the slow growth microorganisms. A schematic of the bioreactor is depicted in FIG. 2. The PVA beads used in the reactor averaged 4.0 mm in diameter, a specific gravity of 1.025, and hydrous ratio (void %) of 90% (Kuraray Co., Osaka, Japan). The reactors had a volume of 1.0 L (6.5 cm diameter glass cylinder). The reactors received a continuous flow of synthetic enrichment medium containing equal amounts of $NH_4$—N and $NO_2$—N. It contained $NH_4Cl$ (variable: 20-300 mg N $L^{-1}$); $NaNO_2$, (variable: 20-300 mg N $L^{-1}$); $KHCO_3$, 125 mg $L^{-1}$; $KH_2PO_4$, 27 mg $L^{-1}$; $FeSO_4 \times 7H_2O$, 9.0 mg $L^{-1}$; EDTA, 5.0 mg $L^{-1}$; $MgSO_4 \times 7H_2O$, 240 mg $L^{-1}$; $CaCl_2 \times 2H_2O$, 143 mg $L^{-1}$; Trace Element Solution, 0.3 mL $L^{-1}$). The trace element solution ($ZnSO_4 \times 7H_2O$, 1247 mg $L^{-1}$; $MnSO_4 \times H_2O$, 1119 mg $L^{-1}$; $CuSO_4 \times 5H_2O$, 44 mg $L^{-1}$; $Al_2(SO_4)_3 \times 14H_2O$, 201.5 mg $L^{-1}$; $Na_2MoO_4 \times 2H_2O$, 129 mg $L^{-1}$; $CoCl_2 \times 6H_2O$, 30 mg $L^{-1}$; KCl, 100 mg $L^{-1}$; EDTA, 975 mg $L^{-1}$). In the first trial, the bioreactor was operated at constant hydraulic retention time (HRT) of 28 hours and a variable influent total N concentration (20-250 mg N/L). In the second trial, the HRT was variable (24 to 12 hours), and influent concentration was constant (300 mg N/L). The carrier beads from this parent reactor were washed to recover the attached anammox bacteria, which was used to inoculate a 10-L pilot reactor. The composition of the synthetic influent was the same as in the parent reactor. The process was optimized when the alkalinity in the influent was adjusted 1:1 with the $NH_4$—N concentration in the influent. $KHCO_3$ added varied with the amount of ammonia in the influent at a rate 2 mg $KHCO_3$ per 1 mg of $NH_4$—N. High amounts of Mg and Ca salts in the synthetic influent also favored isolation of anammox from swine sludges.

In a second phase, a 10-L pilot reactor (9.8 L effective liquid volume) was seeded directly with the anammox red sludge biomass. A total of 111.8 g of wet anammox sludge (2.93 g total solids dry basis) was used. The reactor was configured so that influent synthetic wastewater was injected at the bottom-end of the reactor and treated water was discharged near the top of the reactor after passing through a matrix of immobilized anammox. The glass pilot reactor was jacketed on the outside to control process temperature. Process temperature was maintained at 30° C. with temperature probe inside the reactor and a water heater, controller and circulator. As biomass carrier, the reactor used a polyester non-woven material coated with pyridinium type polymer (Japan Vilene, Tokyo, Japan) designed to enhance retention of microorganisms (Furukawa et al., 2003). The bioreactor was operated over a 3.8-yr period with various hydraulic retention times (HRT 24 to 4 h) and influent total N concentration (40 to 560 mg N/L; 50% as ammonia-N and 50% as nitrite-N).

All water analyses were performed according to Standard Methods for the Examination of Water and Wastewater as disclosed in APHA, AWWA, WEF, 1998. *Standard Methods for the Examination of Water and Wastewater,* $20^{th}$ ed. Washington, D.C.: American Public Health Association, American Water Works Association, and Water Environment Federation and herein incorporated by reference. After filtration through a 0.45-µm membrane filter (Gelman type Supor-450, Pall Corp., Ann Arbor, Mich.), $NH_4$—N was determined by the automated phenate method (Standard Method 4500-$NH_3$ G), $NO_2$—N by the colorimetric method (4500-$NO_2^-$B) $NO_3$—N by the automated cadmium reduction method (Standard Method 4500-$NO_3^-$ F).

Chromosomal DNA Extraction

Sludge samples were retrieved from the pilot anammox bioreactor and the chromosomal DNA was extracted using the ISOPLANT Kit (Nippon Gene, Wako, Osaka, Japan) according to manufacturer's specifications. In short, two solutions I: (50 mM glucose; 25 mM Tris-HCl pH 8.0; 10 mM EDTA pH 8.0) and II: (0.2N NaOH; 1% SDS) were added to sludge samples to precipitate excess cellular constituents (i.e. cell wall, protein). After incubation (15 min at 50° C.), a third solution (5M potassium acetate, 60 mL $L^{-1}$; glacial acetic acid, 11.5 ml $L^{-1}$; water, 28.5 mL $L^{-1}$) was added and incubated on ice for 15 min to allow for DNA dissolution. Cellular debris was removed after centrifugation (14,000 rpm for 15 min at 4° C.), and 99% ice cold ethanol (1 mL) was added to the remaining supernatant to allow for DNA precipitation. After a second round of centrifugation, the precipitated DNA was cleaned with 70% ethanol, vacuum-dried, re-eluted in TE Buffer (Tris-HCl, 12.1 g $L^{-1}$; EDTA, 0.37 g $L^{-1}$), and stored at 4° C. DNA quality and quantity were assessed using 1% agarose gel. The gel was stained with SYBR-Gold solution (Invitrogen Corp., Carlsbad, Calif.), and visualized as a 16-bit gray-scale image using FLA-2000 system (Fuji Photo Film Co., Ltd., Tokyo, Japan).

PCR Amplification of Chromosomal DNA

Ribosomal DNA gene (16S) was amplified from the chromosomal DNA using the PCR primer set 16S-5'II/16S-3' according to Fujii et al. (2002). A 50-µL reaction volume composed of the following PCR mix was used for 16S amplification: chromosomal DNA (10 ng), 1 µL; 16S-5'II, 2 µL (5 pmol); 16S 3', 2 µL (5 pmol); KOD-Plus taq polymerase (Takara Bio, Inc., Otsu, Shiga, Japan), 1 µL; 10× PCR Buffer for KOD-Plus (Takara), 5 µL; dNTPs (2 mM), 5 µL; MgSO4 (25 mM), 2 µL; PCR-water, 32 µL. The PCR cycling conditions were as follows: 94° C. for 2 min, followed by 30 cycles of 94° C. for 15 sec (denaturation), 57° C. for 2 sec (primer annealing), 68° C. for 30 sec (extenstion). Amplified 16S DNA samples were electrophoresed on 1.5% agarose gels, and PCR products from the gel were excised and purified using the QIAquick PCR purification Kit (Qiagen, Valencia, Calif.), according to manufacturer's specifications.

Cloning of Amplified DNA

Amplified 16S DNA and linearized vector DNA (HincII-digested pBluescript SKII(+); Stratagene, La Jolla, Calif., USA) were purified using the QIAprep Spin Miniprep Kit (Qiagen). Using the Takara DNA Liagtion Kit, ver. 2 (Takara), the purified 16S and vector DNA were ligated together and then cloned into competent *E. coli* cells, according to manufacturer's specifications. Prior to cell spreading, 40 μL of both X-Gal (5-bromo-4-chloro-3-indolyl-β-D-galactopyranoside; 20 mg mL$^{-1}$) and IPTG (isopropyl-β-D-galactoside; 20 mg mL$^{-1}$) substrates were added to the surface of the plates to allow for selection of correct *E. coli* cells. Cloned *E. coli* cells were incubated (37° C.) overnight on LB+Amp agar plates (Polypeptone, 10 g L$^{-1}$; Yeast extract, 5 g L$^{-1}$; NaCl, 5 g L$^{-1}$; Ampicillin sodium, 0.1 g L$^{-1}$; Agar 15 g L$^{-1}$), and white cell colonies (correct transformants) were aseptically removed from the plates and inoculated into LB+Amp liquid media (Polypeptone, 10 g L$^{-1}$; Yeast extract, 5 g L$^{-1}$; NaCl, 5 g L$^{-1}$; Ampicillin sodium, 0.1 g L-1) and incubated overnight at 37° C. Plasmid DNA was extracted and PCR amplified according to the protocols described above, with two exceptions. During the plasmid DNA extraction, a fourth solution (24:1 Chloroform:Isoamyl Alcohol) was added to the extraction mixture prior to centrifugation to remove cellular debris. The second exception was the PCR reaction mixture used for the extracted plasmid DNA: Plasmid DNA (1:50 dilution of extract), 1 μL; 16S-5'II, 1 μL (5 pmol); 16S 3', 1 μL (5 pmol); KOD-Plus taq polymerase (Takara Bio, Inc., Otsu, Shiga, Japan), 0.5 μL; 10×PCR Buffer for KOD-Plus (Takara), 5 μL; dNTPs (2 mM), 5 μL; MgSO4 (25 mM), 2 μL; PCR-water, 34.5 μL. The PCR cycling conditions remained the same. Grouping of Cloned PCR Products by Restriction Fragment Length Polymorphism (RFLP) and Sequencing of Cloned PCR Products To assess the diversity of the clones, the PCR product obtained from each clone was digested with each one of three endonucleases (HaeIII, RsaI, Sau3AI) to produce restriction fragment length polymorphism (RFLP) fingerprint patterns that could be compared among clones to determine diversity. The following RFLP reaction mixture was used: Clone PCR product, 5 μL; endonuclease (HaeIII, RsaI, or Sau3AI), 0.5 μL; 10×M-buffer, 1 μL; PCR water, 3.5 μL. After 1 h incubation (37° C.), digested DNA was analyzed using a 1.5% agarose gel, and the RFLP fingerprint patterns from the different clones were compared. DNA sequences of the clones were obtained using the DYEnamic ET Terminator Cycle Sequencing Kit (Amersham Pharmacia Biotech, Piscataway, N.J., USA) in conjunction with a 3130×1 genetic analyzer (Applied Biosystems, Foster City, Calif., USA), and performed according to manufacturer's specifications.

The clone PCR product sequences were submitted to the blast search engine of the GenBank database (Altschul et al., 1997) to obtain putative phylogenetic assignment for each clone. These sequences, combined with the closest sequence matches and known anammox sequences from the GenBank database, were aligned using MEGA v. 4.0 (Tamura et al., 2007) The alignment files were used to create bootstrapped (n=1000) consensus neighbor joining trees, using the Kimura-2-parameter model in the MEGA v. 4.0 software package.

EXAMPLE 1

Anammox Enrichment

In the first trial, the anammox reaction was first noticeable at day 490 with simultaneous removal of $NO_2^-$ and $NH_4^+$. At the same time, a distinct red biomass growth, which is typical of the anammox planctomycetes bacteria, colonized the PVA hydrogel biomass carrier beads. These developments occurred only when high N (>200 mg/L) and adequate salt strength was used in the synthetic media. Under the conditions and protocol determined in trial one, it took about 100 days in trial two to develop the anammox reaction from sludges obtained from swine farms in USA. Nitrogen removal rates obtained during first-phase development were 0.4 to 0.5 kg N/m$^3$/day, which are already in the range of industrial bio-treatment applications. These rates compare to reported removal rates for conventional nitrification/denitrification for industrial applications (e.g. treatment of effluents from anaerobic digestors, rendering plants or landfill leachate). Removal of $NO_2^-$ and $NH_4^+$ in the parent reactor was simultaneous at the stoichiometric ratios as: $NH_4^+ + 1.24$ $NO_2^- \rightarrow 1.00$ $N_2 + 0.24$ $NO_3^-$. Fluorescence In-situ hybridization (FISH) analysis of the biofilm was performed using 16S rDNA oligonucleotides probe FLO-1 derived from the sequence in FIG. 1 and a confocal microscope. The imaging thus obtained revealed a high density of cells growing in clusters, which is characteristic of anammox bacteria.

EXAMPLE 2

Pilot Reactor

Figure 3:
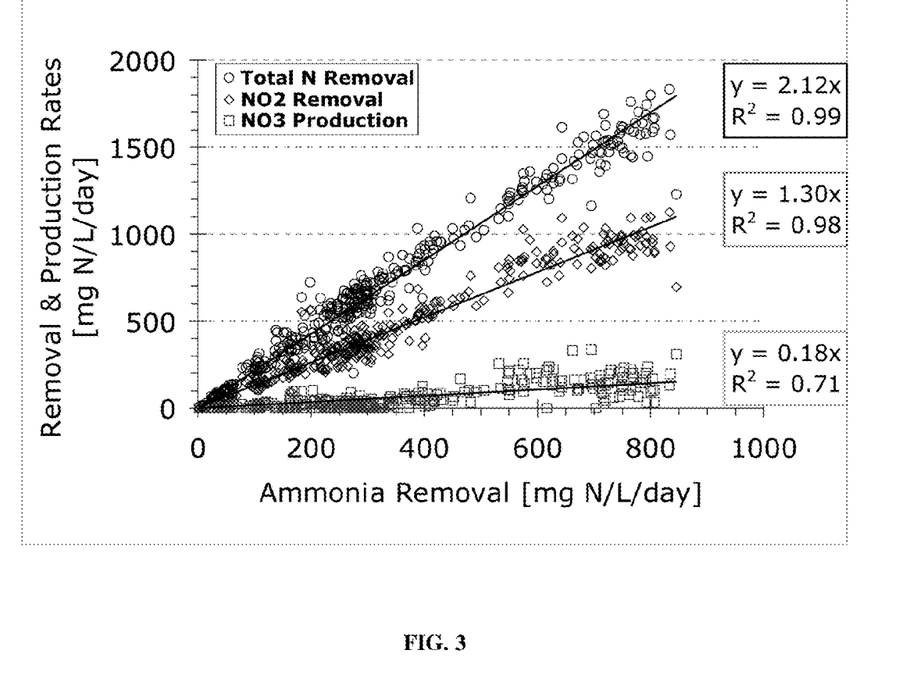
FIG. 3 is a graph depicting the stoichiometric ratio of the anammox reaction in the pilot reactor using anammox bacterium NRRL B-50286 using various hydraulic retention times (HRT 24 to 4 h) and influent total N concentration.

Removal of $NO_2^-$ and $NH_4^+$ at typical stoichiometric ratios of the anammox reaction occurred from day 1 of operation of the pilot reactor seeded with the enriched anammox sludge generated in the previous trials. Nitrogen removal rates increased quickly with time in the pilot reactor seeded with the anammox enriched sludge (FIG. 3). Nitrogen removal rate increased linearly from 0 to 600 mg N/L-reactor/day in the first 4 months of operation (rate increase 4.8 mg N/L/day per day; $R^2$=0.92). The total N removal rates up to about 1830 mg N/L-reactor/day (1.8 kg N/m3/day) were obtained. Removal of $NO_2^-$ and $NH_4^+$ was simultaneous at the stoichiometric ratios summarized as $NH_4^+ + 1.30$ $NO_2^- \rightarrow 1.06$ $N_2 + 0.18$ $NO_3^-$. These ratios were obtained during operation of the reactor shown in FIG. 3 from the linear relationships between total N removal per unit of ammonia N removal (2.12 or 1.06 $N_2$), nitrite N removal per unit of ammonia N removal (1.30), and nitrate N produced per unit of ammonia N removal (0.18).

Data in Table 2 summarize stabilized performance obtained with NRRL B-50286 in a continuous flow pilot reactor during 350 days of nonstop operation. The hydraulic retention time (HRT) was 3.9 hours. The average total N loading rate was 1.74 kg N/m$^3$/day and the total N removal rate was 1.48 kg N/m$^3$/day. At these high mass N loading, the average removal efficiency obtained was 85%. Similarly, the ammonia and nitrite were removed at efficiencies of 89 and 98%, respectively (Table 2).

TABLE 2

Removal of wastewater nitrogen using strain NRRL B-50286 in upflow continuous pilot reactor[a]

| | Mass Nitrogen | | | Removal |
|---|---|---|---|---|
| | Influent[b] | Effluent | Removal | Efficiency |
| | | mg N L$^{-1}$ d$^{-1c}$ | | % |
| Total N[d] | 1,735 ± 137 | 260 ± 122 | 1,477 ± 168 | 85 ± 7 |
| Ammonia | 804 ± 80 | 92 ± 71 | 709 ± 88 | 89 ± 9 |
| Nitrite | 930 ± 80 | 22 ± 47 | 915 ± 90 | 98 ± 5 |
| Ammonia + Nitrite | 1,735 ± 138 | 114 ± 101 | 1,621 ± 155 | 94 ± 6 |

[a]The reactor was operated continuously at a flow rate of 60 L d$^{-1}$. Effective liquid volume of the pilot reactor was 9.8 L and the hydraulic retention time (HRT) was 3.9 hours.
[b]Influent wastewater containing 283.4 ± 22.4 mg-N L$^{-1}$ (131.4 ± 13.0 mg $NH_4$—N L$^{-1}$, 152.0 ± 13.0 mg $NO_2$—N L$^{-1}$, and 0.1 ± 0.6 mg $NO_3$—N L$^{-1}$).
[c]Data are average ± standard deviation of 61 samples collected over a 350-day continuous period.
[d]Total Nitrogen = Ammonia ($NH_4$—N) + Nitrite ($NO_2$—N) + Nitrate ($NO_3$—N).

Anammox bacteria were successfully isolated from animal waste sludge using immobilizing techniques and continuous flow reactors. Anammox reaction startup was favored by high nitrogen influent concentrations. Average nitrogen removal rates obtained were 1.5 kg N/m$^3$-reactor/day with loading rates of 1.7 kg N/m$^3$-reactor/day and HRT of 3.9 hours.

EXAMPLE 3

Preservation and Reactivation of Procedures for NRRL B-50286

In order to demonstrate that strain NRRL B-50286 can survive various preservation techniques, strain NRRL B-50286 was subjected to a four month preservation period that included refrigeration in nitrate media at 4° C., lyophilization in skim milk media with strain pre-frozen at −60° C., lyophilization in skim milk media with samples pre-frozen using liquid nitrogen (−200° C.). Following the preservation period, the strain was reactivated and tested for anammox activity with the bioreactor as disclosed in Example 2.

For refrigerated samples, 10 g of biomass from the pilot anammox reactor was placed in 50-mL glass screw cap centrifuge tubes (Corning Inc., Corning, N.Y.) and the remaining headspace in the tube was filled with N$_2$-bubbled nitrate solution (KNO$_3$, 80 mg L$^{-1}$). Caps with silicon septa were used to anaerobically seal the centrifuge tubes, and the media was replaced monthly, according to published anammox preservation protocol as described in Vlaeminck et al., (2007) Reactivation of aerobic and anaerobic ammonium oxidizers in OLAND biomass after long-term storage. *Appl. Microbiol. Biotechnol.* 74:1376-1384, and incorporated herein by reference. For lyophilized samples, 2.5 g of biomass was homogenously mixed with 12.5 mL of sterile skim milk media (20 g 100 mL$^{-1}$; B-D, Franklin Lakes, N.J.) in 50 mL polypropylene centrifuge tubes (VWR) and frozen prior to lyophilization at −60° C. in an ultra-low freezer, or in liquid nitrogen (−200° C.). Using a Labconco FreeZone 4.5 L freeze dryer (Labconco Corp., Kansas City, Mo.), pre-frozen samples were lyophilized (−50° C., <0.04 mbar) until all water was removed from the biomass (3-5 days).

Preserved anammox bacteria were reactivated in N$_2$-bubbled reactivation media specially formulated for the growth of strain NRRL B-50286 (NH$_4$Cl, 382 mg L$^{-1}$; NaNO$_2$, 493 mg L$^{-1}$; KHCO$_3$, 200 mg L$^{-1}$; KH$_2$PO$_4$, 27 mg L$^{-1}$; FeSO$_4$×7H$_2$O, 9.0 mg L$^{-1}$; EDTA, 5.0 mg L$^{-1}$; MgSO$_4$×7H$_2$O, 240 mg L$^{-1}$; CaCl$_2$×2H$_2$O, 143 mg L$^{-1}$; Trace Element Solution, 0.3 mL L$^{-1}$). The trace element solution (ZnSO$_4$×7H$_2$O, 1247 mg L$^{-1}$; MnSO$_4$×H$_2$O, 1119 mg L$^{-1}$; CuSO$_4$×5H$_2$O, 44 mg L$^{-1}$; Al$_2$(SO$_4$)$_3$×14H$_2$O, 201.5 mg L$^{-1}$; Na$_2$MoO$_4$×2H$_2$O, 129 mg L$^{-1}$; CoCl$_2$×6H$_2$O, 30 mg L$^{-1}$; KCl, 100 mg L$^{-1}$; EDTA, 975 mg L$^{-1}$) provided micronutrients required for microbial growth. After storage (4 months), preserved anammox bacteria were washed 5-7 times in 40-50 mL of N$_2$-bubbled reactivation media to remove any residual nitrate (refrigerated preservation technique) or skim milk (lyophilized preservation techniques) media. The washed anammox bacteria were transferred into a 60 mL glass centrifuge tube (Corning, Inc.) and completely filled with N$_2$-bubbled reactivation media. Duplicate anammox samples were then incubated anaerobically in a shaking water bath (34° C. @ 75 r.p.m.) for 1 week to reactivate the preserved anammox bacteria.

After the 1-week activation period, the growth media was replaced with fresh N$_2$-bubbled reactivation media. Sealed centrifuge tubes were mixed and 3 mL of growth media was removed from the tubes using a 22 G1.5 needle (B-D) attached to a 10 mL syringe (B-D). The volume of sample removed from the sealed tube was replaced with an equivalent volume of N$_2$ to maintain an anaerobic environment. The N$_2$ gas was transferred through a 22 G1.5 needle connected via Tygon tubing (Cole-Parmer, Vernon Hills, Ill.) to a 5-L gas-tight Tedlar bag (Cole-Parmer). Liquid media samples were filtered using a 1.5 μm glass fiber 25 mm syringe filter (Environmental Express, Mount Pleasant, S.C.) and were analyzed colorimetrically with an AutoAnalyzer II (Technicon Instruments Corp., Tarrytown, N.Y.) using Standard Methods 4500-NH$_3$ for NH$_4$—N and 4500-NO$_3^-$ for NO$_2$—N and NO$_3$—N as described in *Standard Methods for the Examination of Water and Wastewater.* 1998, Am. Public Health Assoc., Washington, D.C., and incorporated herein by reference. The analyses of these first samples determined the starting concentrations for each nitrogen species, and were compared with subsequent samplings to determine anammox activity. Liquid samples were analyzed on a daily (refrigerated samples) or weekly (lyophilized samples) basis to determine how much NH$_4$—N and NO$_2$—N has been consumed and how much NO$_3$—N has been produced, relative to the starting concentrations. Reactivation of strain NRRL B-50286 was detected when the following stoichiometric ratios of NH$_4^+$+ 1.30 NO$_2^-$→1.06 N$_2$+0.18 NO$_3^-$ was constant during two consecutive sampling periods: Total N Removed/NH$_3$ Removed=2.12; NO$_2$ Removed/NH$_3$ Removed=1.30; NO$_3$ Produced/NH$_3$ Removed=0.18.

Figure 5A:
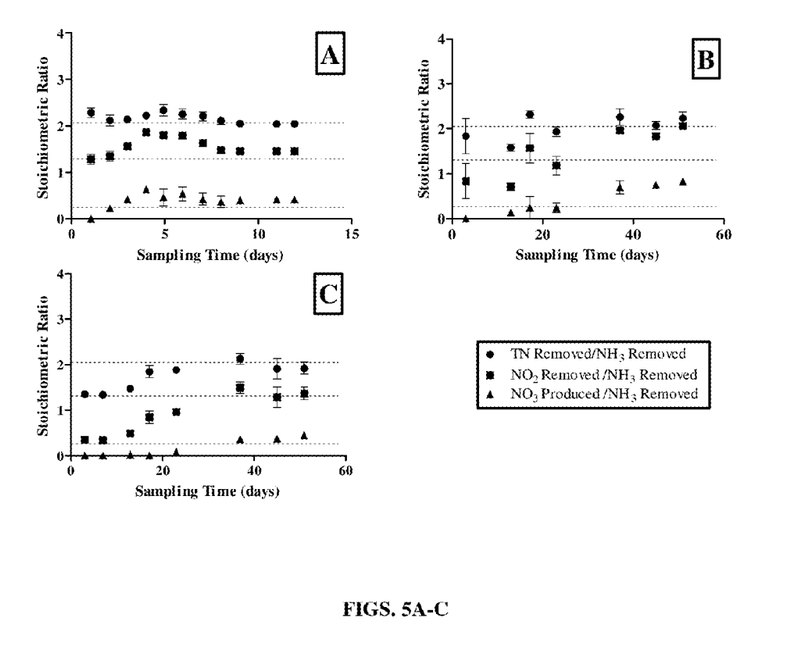
Figure 6:
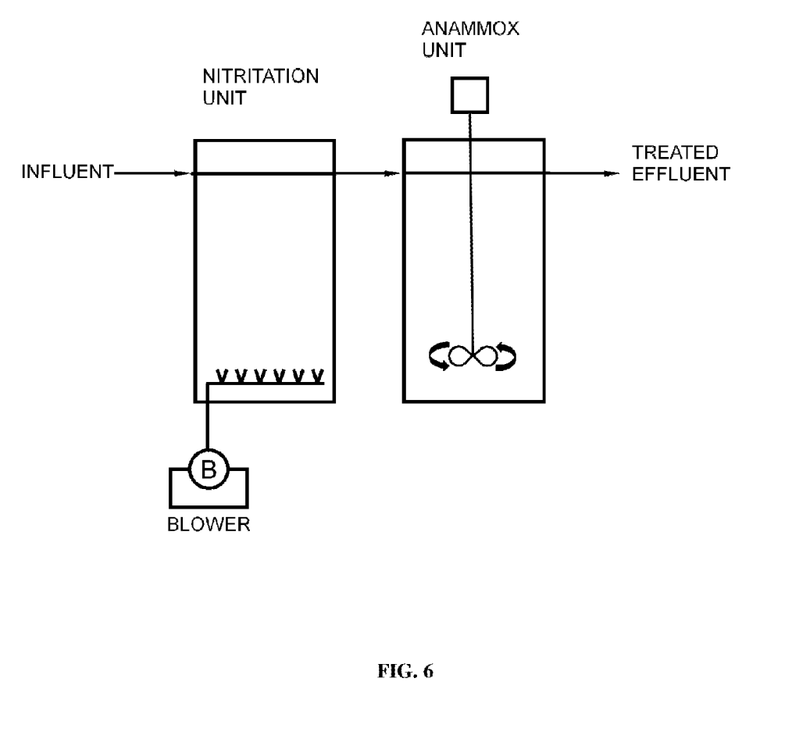
FIG. 6 is a schematic diagram for a two-stage wastewater treatment system combining partial nitrification (nitritation) and anammox for treating ammonium.
Figure 7:
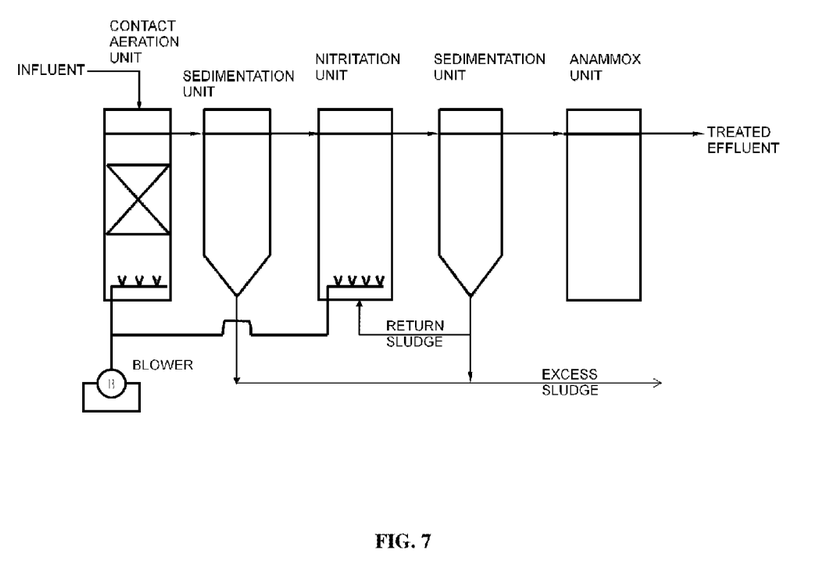
FIG. 7 is a schematic diagram for a two-stage nitritation and anammox wastewater treatment system with contact aeration unit to reduce wastewaters containing biological oxygen demand (BOD) components and sedimentation units to reduce particulates. This is illustrative of unit processes for the removal of biodegradable organic materials contributing to BOD before the autotrophic nitrogen removal through partial nitritation and anammox.

According to FIG. 5 A-C, refrigerated strain NRRL B-50286 stored in a nitrate media for four months resumed anammox activity after one week of incubation in the anammox reactivation media (FIG. 5A). Samples treated by pre-freezing at −60° C. in skim milk prior to lyophilization failed to reactivate, showing much higher stoichiometric ratios than those expected for the anammox reaction (FIG. 5B). However, samples preserved in skim milk media and pre-frozen using liquid nitrogen (−200° C.) prior to lyophilization resumed normal anammox activity after 5 weeks (FIG. 5C). Surprisingly this is the first case of an anammox bacterium being successfully reactivated after preservation using lyophilization and subsequent long-term storage. There was no difference between the stoichiometric ratios demonstrated by the refrigerated or liquid nitrogen lyophilization techniques, and considering the ease of transport and storage of lyophilized samples (no special storage or handling conditions are required), lyophilization in skim milk media using liquid nitrogen is considered a preferred method for the preservation, long-term storage, and transport of anammox bacteria.

EXAMPLE 4

Specific Activity of NRRL B-50286 in 3-Liter Reactor

The specific activity of the anammox sludge NRRL B-50286 was determined using a 3-liter anaerobic jacketed glass reactor (Chemglass Life Sciences, Vineland, N.J., USA), which was operated in batch mode. The 3-liter reactor used 600 mL of the red anammox biomass which was developed and collected from inside the 10-L pilot reactor described supra. The anammox sludge had a granular structure with granules measuring 2-4 mm. After harvesting of the sludge, it was transferred immediately into the 3-L reactor and mixed with wastewater. The mixed liquor was bubbled for 5 minutes with N$_2$ gas (1000 ml/min) to reduce dissolved oxygen concentration to <1 ppm. The reactor was then sealed and tested under anaerobic conditions. The concentration of suspended biomass inside the 3-liter reactor was 2,645 mg volatile suspended solids (VSS) per liter and 3,254 mg total suspended solids (TSS) per liter. Initial concentrations of ammonia and nitrite in the synthetic wastewater at the beginning of the batch test were 58 and 72 mg N/L, respectively. During the test, the reactor was mixed using a stirrer (Opti-Chem) operated at 55 rpm. The process temperature was 32.5° C. The specific activity test of the sludge, conducted in duplicate, lasted 1.5 hours. Liquid samples were extracted through a sampling port every 20 minutes to determine the changes in $NH_4$—N, $NO_2$—N and $NO_3$—N concentration as a function of time as disclosed in FIG. 10. The slope of the regression lines relating N concentration and time indicated the rates of N transformations in the reactor in mg N/L-reactor/hour. The specific activity of the anammox sludge, expressed as mg N removal/mg VSS (biomass)/day, was calculated from the rates of N removal obtained (mg of N removal/L-reactor/hour) and the concentration of anammox biomass measured in the reactor (mg VSS/L-reactor).

Figure 10:
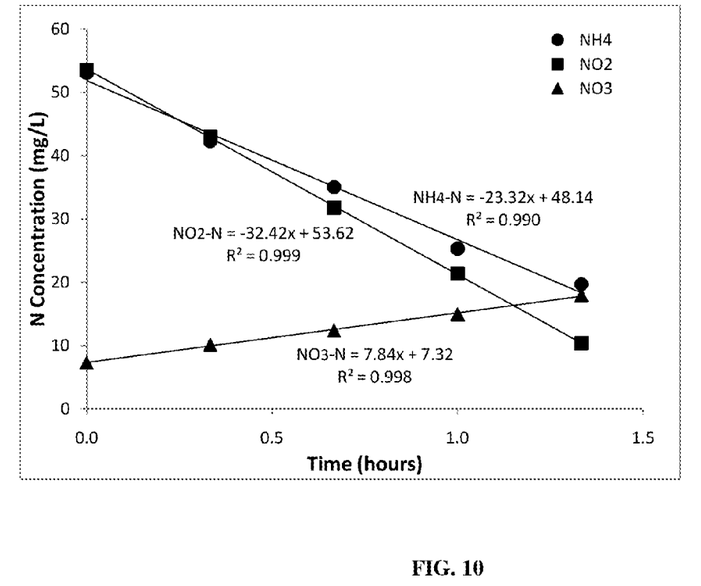
FIG. 10 discloses a graph showing changes in ammonia, nitrite, and nitrate concentrations in wastewater as a function of time using suspended anammox bacterium NRRL B-50286 in a 3-L batch reactor.

FIG. 10 shows the results of batch trials used to determine the specific activity of the anammox sludge for strain NRRL B-50286. The test was done in a 3-L glass reactor containing wastewater and 600 mL of suspended anammox sludge (final sludge concentration=2,645 mg VSS/L). The volumetric rates of N transformations in the reactor (slope of the regression lines) were: $NH_4$—N removal=23.32 mg N/L-reactor/hour; $NO_2$—N removal=32.42 mg N/L-reactor/hour; and NO3-N production=7.84 mg N/L-reactor/hour. Therefore, the rate of ammonia+nitrite removal in the suspended batch reactor was 55.74 mg N/L-reactor/hour (1,337.8 mg N/L-reactor/day), and the rate of total N removal was 47.90 mg N/L-reactor/hour (1,149.6 mg N/L-reactor/day). The specific activity of the anammox sludge obtained was 0.506 mg N/mg VSS/day for ammonia+nitrite removal, and 0.435 mg N/mg VSS/day for total N removal.

While the invention has been described with reference to details of the illustrated embodiment, these details are not intended to limit the scope of the invention as defined in the appended claims.

The embodiment of the invention in which exclusive property or privilege is claimed is defined as follows:

1. An isolated anaerobic ammonium oxidating bacterium capable of oxidizing ammonium and releasing di-nitrogen gas identified as *Candidatus Brocadia caroliniensis* having Accession Deposit Number NRRL B-50286.

2. The bacterium of claim 1 wherein, the bacterium is capable of reactivation after lyophilization.

3. The bacterium of claim 1 having ribosomal DNA of SEQ. ID. NO. 1.

4. A wastewater treatment composition comprising:
(a) the isolated anaerobic ammonium oxidating bacterium *Candidatus Brocadia caroliniensis* having Accession Deposit Number NRRL B-50286 in amounts effective to reduce levels of ammonia and release di-nitrogen; and
(b) a suitable carrier.

* * * * *